US012797417B2

(12) United States Patent
Lee et al.

(10) Patent No.: US 12,797,417 B2
(45) Date of Patent: Nov. 17, 2026

(54) METHOD FOR STERILIZING BONE GRAFT MATERIAL

(71) Applicant: Cellumed Co., Ltd., Seoul (KR)

(72) Inventors: Jung Soo Lee, Suwon-si (KR); Keun-Soo Lee, Goyang-si (KR); Young Mo Kang, Bucheon-si (KR); Yong Woo Lim, Bucheon-si (KR); Ju Woong Jang, Seoul (KR)

(73) Assignee: Cellumed Co., Ltd, Seoul (KR)

( * ) Notice: Subject to any disclaimer, the term of this patent is extended or adjusted under 35 U.S.C. 154(b) by 486 days.

(21) Appl. No.: 17/899,089

(22) Filed: Aug. 30, 2022

(65) Prior Publication Data

US 2023/0241120 A1 Aug. 3, 2023

(30) Foreign Application Priority Data

Aug. 30, 2021 (KR) ........................ 10-2021-0114880

(51) Int. Cl.

| | |
|---|---|
| ***A61K 35/32*** | (2015.01) |
| ***A61K 33/42*** | (2006.01) |
| ***A61K 41/17*** | (2020.01) |
| ***A61K 47/38*** | (2006.01) |
| ***A61L 2/081*** | (2026.01) |
| ***A61L 103/05*** | (2026.01) |

(52) U.S. Cl.

CPC .............. *A61K 35/32* (2013.01); *A61K 33/42* (2013.01); *A61K 41/17* (2020.01); *A61K 47/38* (2013.01); *A61L 2/081* (2013.01); *A61L 2103/05* (2026.01)

(58) Field of Classification Search

None

See application file for complete search history.

(56) References Cited

U.S. PATENT DOCUMENTS 9,132,208 B2 * 9/2015 Chen .................... A61L 27/3604
2013/0095183 A1 * 4/2013 Gibson ................. A61L 27/425
424/602

OTHER PUBLICATIONS

Shallenberger, M. et al (2016) The effect of temperature exposure during shipment on a commercially available demineralized bone matrix putty. Cell Tissue Bank. Aug. 17:677-687 (Year: 2016).*
Folsch, C. et al (2012) Effect of Storage Temperature on Allograft Bone. Transfus Med Hemother. Feb: 39(1):36-40. (Year: 2012).*

* cited by examiner

*Primary Examiner* — Allison M Fox
*Assistant Examiner* — Marisol Ann O'Neill
(74) *Attorney, Agent, or Firm* — Sughrue Mion, PLLC

(57) ABSTRACT

The present invention relates to a method for sterilizing a bone graft material, and more specifically, to a method for sterilizing a bone graft material containing sodium carboxymethyl cellulose (CMC) gel without changing its properties.

5 Claims, 14 Drawing Sheets

[DBM-CMC 3% (40:60]

RT gamma frozen gamma

DBM : CMC and water
= 80 : 20 wt%

DBM : CMC and water
= 60 : 40 wt%

METHOD FOR STERILIZING BONE GRAFT MATERIAL

TECHNICAL FIELD

The present invention relates to a method for sterilizing a bone graft material, and more specifically, to a method for sterilizing a bone graft material containing sodium carboxymethyl cellulose (CMC) gel without changing its properties.

BACKGROUND ART

A hydrogel is a polymeric material having a three-dimensional network structure that can contain a large amount of water, and exhibits characteristics similar to those of living tissue due to its flexible strength and high water content. Due to these characteristics, the hydrogel has been widely used in the medical or pharmaceutical field. Recently, by developing various types of hydrogels, attempts for tissue engineering treatment for bone defects have been actively made.

Particularly, in case of transplanting a bone graft material to a desired site, it is required for the material to have excellent properties that can minimize bone loss after washing, be easily changed into any shape, and be easily engrafted. A carrier is very important to maintain these properties since physical handling properties such as fluidity and viscosity may vary depending on the properties of material.

In addition, for transplantation, microorganisms must be completely killed, and the Sterility Assurance Level (S.A.L) must be managed to meet the sterilization conditions of $10^{-6}$ or less. As a sterilization method, an EO gas sterilization method is widely used, but has a problem that it is effective only for removing microorganisms present on the surface of material.

As another sterilization method, gamma irradiation has been suggested as an alternative. However, since the properties of the bone graft material before sterilization are altered by the gamma irradiation, a serious problem occurs in an actual transplantation.

Therefore, a demand for a method capable of minimizing a change in physical properties of bone graft material even after sterilization has been continuously raised in the art.

Technical Problem

The inventors have experimentally demonstrated that, when a bone graft material is sterilized by gamma irradiation commonly used, its physical properties may not be altered by performing a pretreatment at a specific temperature. Accordingly, the present invention has been completed.

Technical Solution

The present invention provides a method for sterilizing a bone graft material comprising a demineralized bone matrix and a carboxymethyl cellulose salt, comprising:

a) preparing a bone graft material by mixing a demineralized bone matrix and a carboxymethyl cellulose salt;
b) pretreating the bone graft material prepared in step a) by maintaining it at a temperature below 0° C.; and
c) sterilizing the bone graft material pretreated in step b) by gamma irradiation.

In one embodiment of the invention, the pretreatment of step b) is performed at a temperature of −20° C. or less.

In one embodiment of the invention, the bone graft material of step a) further comprises hydroxyapatite. In addition, any materials commonly used for bone grafting may be further comprised.

In one embodiment of the invention, the carboxymethyl cellulose salt in step a) is, but not limited to, sodium carboxymethyl cellulose.

In one embodiment of the invention, the step c) is performed by gamma irradiation in 25 to 40 kGy, but not limited thereto.

In one embodiment of the invention, the bone graft material obtained through sterilization in step c) may be used to transplant into a human bone defect site.

When a bone graft material is conventionally sterilized by gamma irradiation, its inherent properties are deteriorated. Accordingly, even though microorganisms are killed, there is a serious problem of deterioration in properties that makes it unsuitable for transplantation. However, if the bone graft material is sterilized by gamma irradiation after pre-freezing treatment according to the method of the present invention, its properties before sterilization can be maintained almost intact.

When the bone graft material sterilized according to the method of the present invention is used, it is well aggregated with strong cohesion, and has excellent properties of maintaining its shape. In addition, it can be easily changed into any shape, and thus this makes it possible to flexibly change the shape tailored to the implantation site. Moreover, the bone graft material does not adhere well on the hand or device during the transplantation process, and thus bone loss is minimized, and engraftment can be performed in an intact form.

These advantages allow a doctor in orthopedic surgery or dentistry to engraft the bone graft material while transforming it into a shape suitable for the corresponding site, and minimizing or preventing bone loss.

A term used herein include singular or plural meanings. For example, "component" means one component or at least one component.

EXAMPLES

Figure 1:
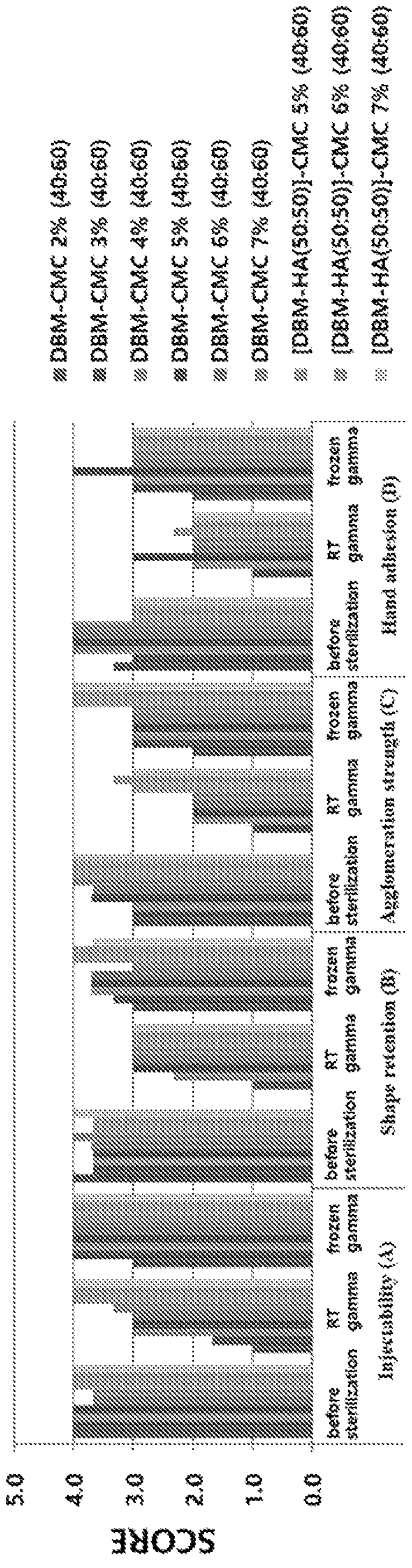
FIG. 1 is a graph showing the results of scoring for physical properties of bone regeneration compositions in various mixing ratios before sterilization, after room temperature gamma sterilization, and after frozen gamma sterilization.
Figure 2:
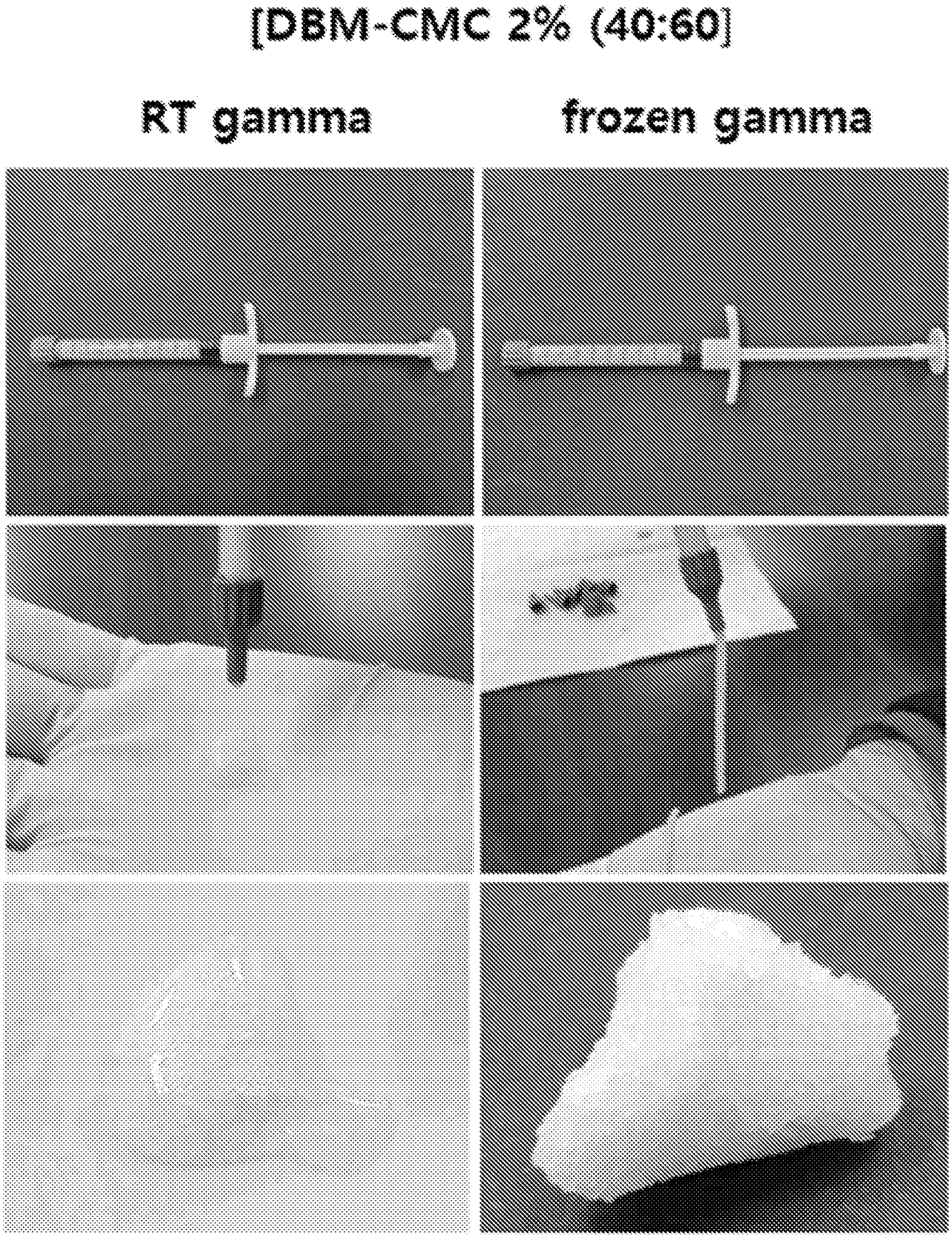
FIGS. 2 to 10 are photographs showing the state filled in the syringe, the state being ejected from the syringe, and the state after ejected from the syringe, respectively, for the samples prepared in Examples 1 to 9.
Figure 3:
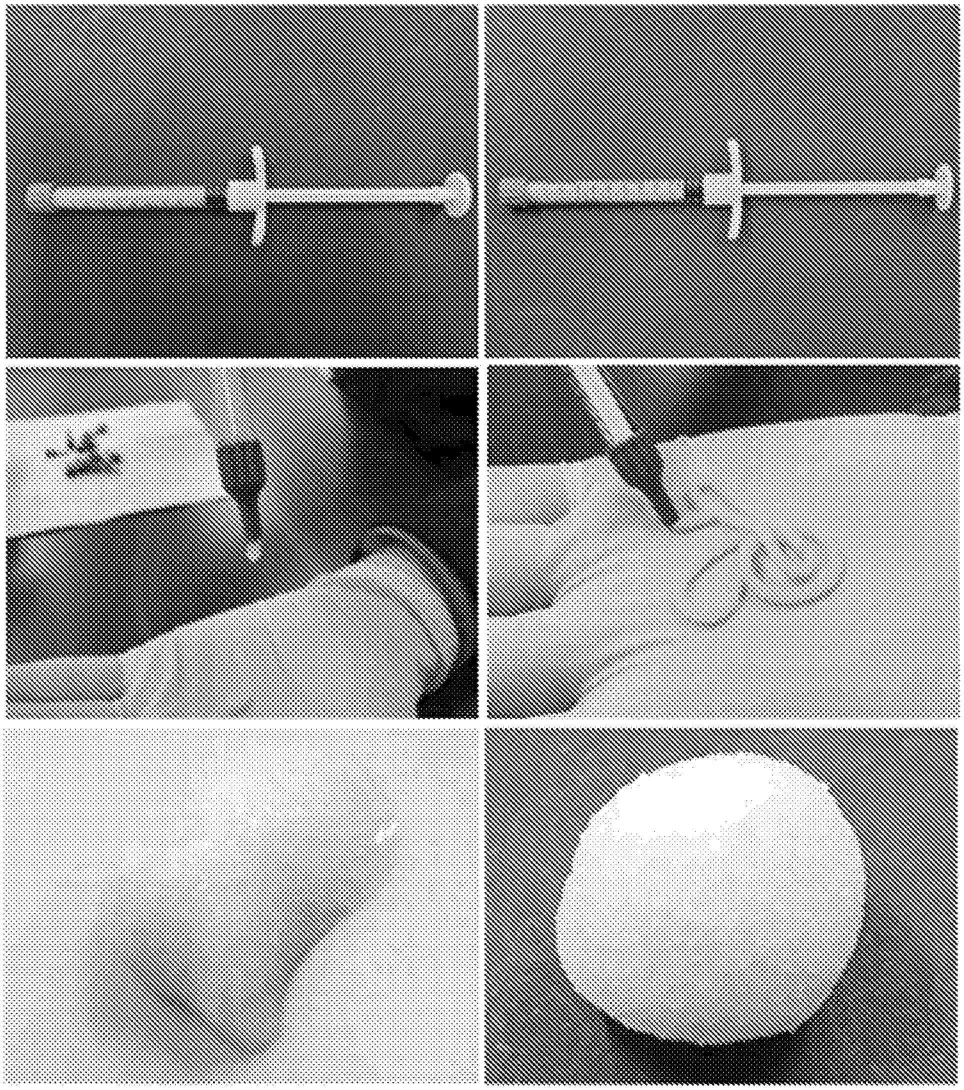
Figure 4:
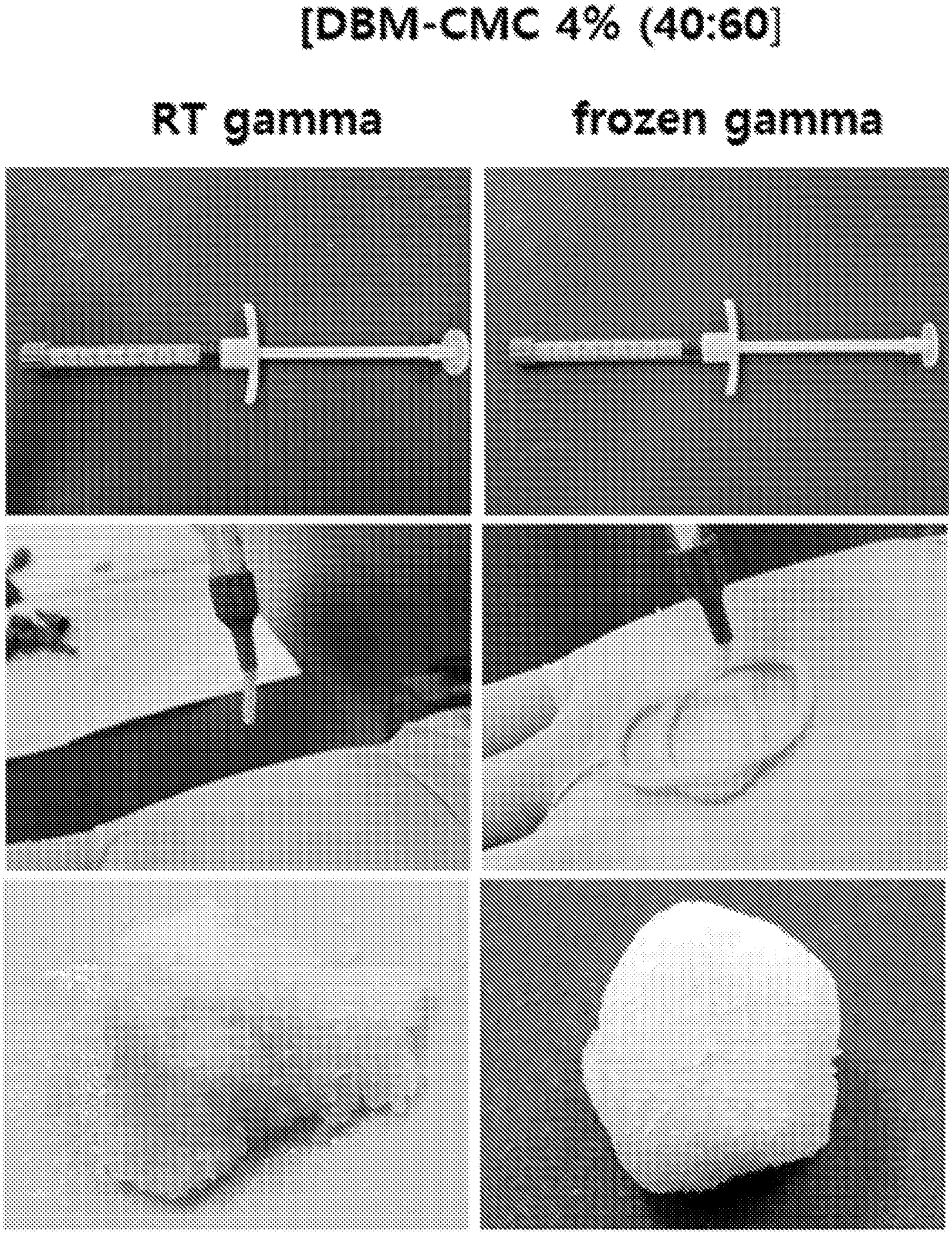
Figure 5:
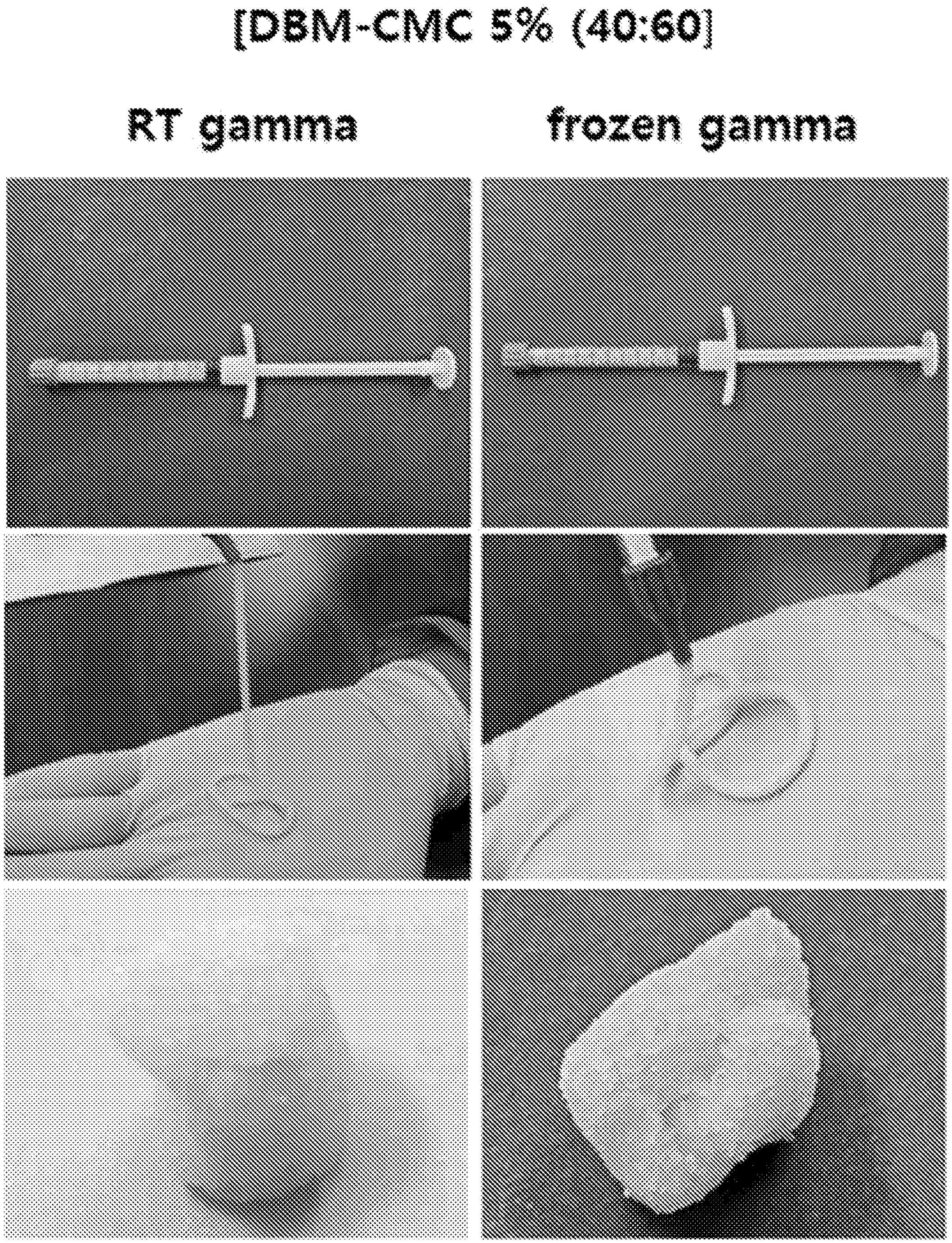
Figure 6:
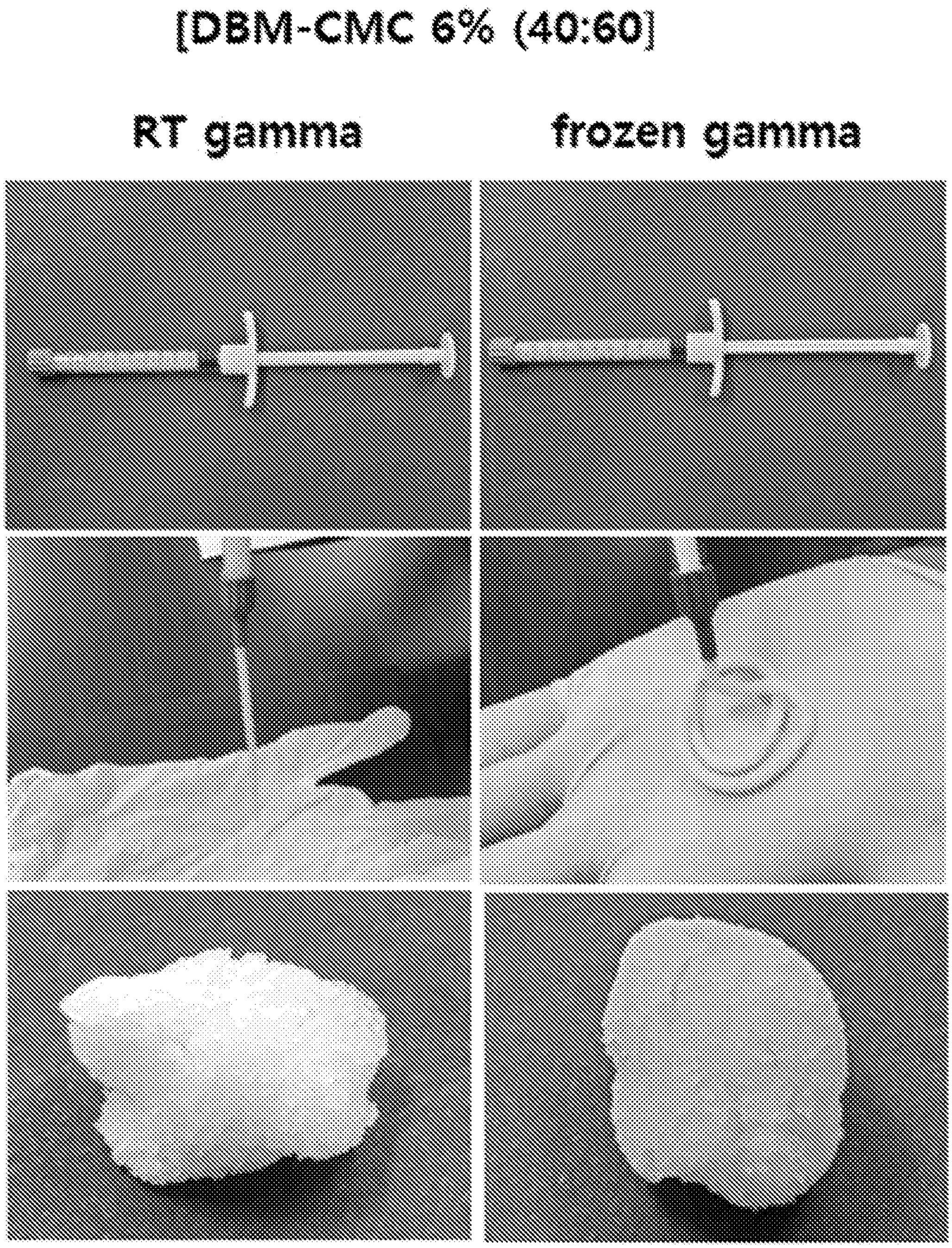
Figure 7:
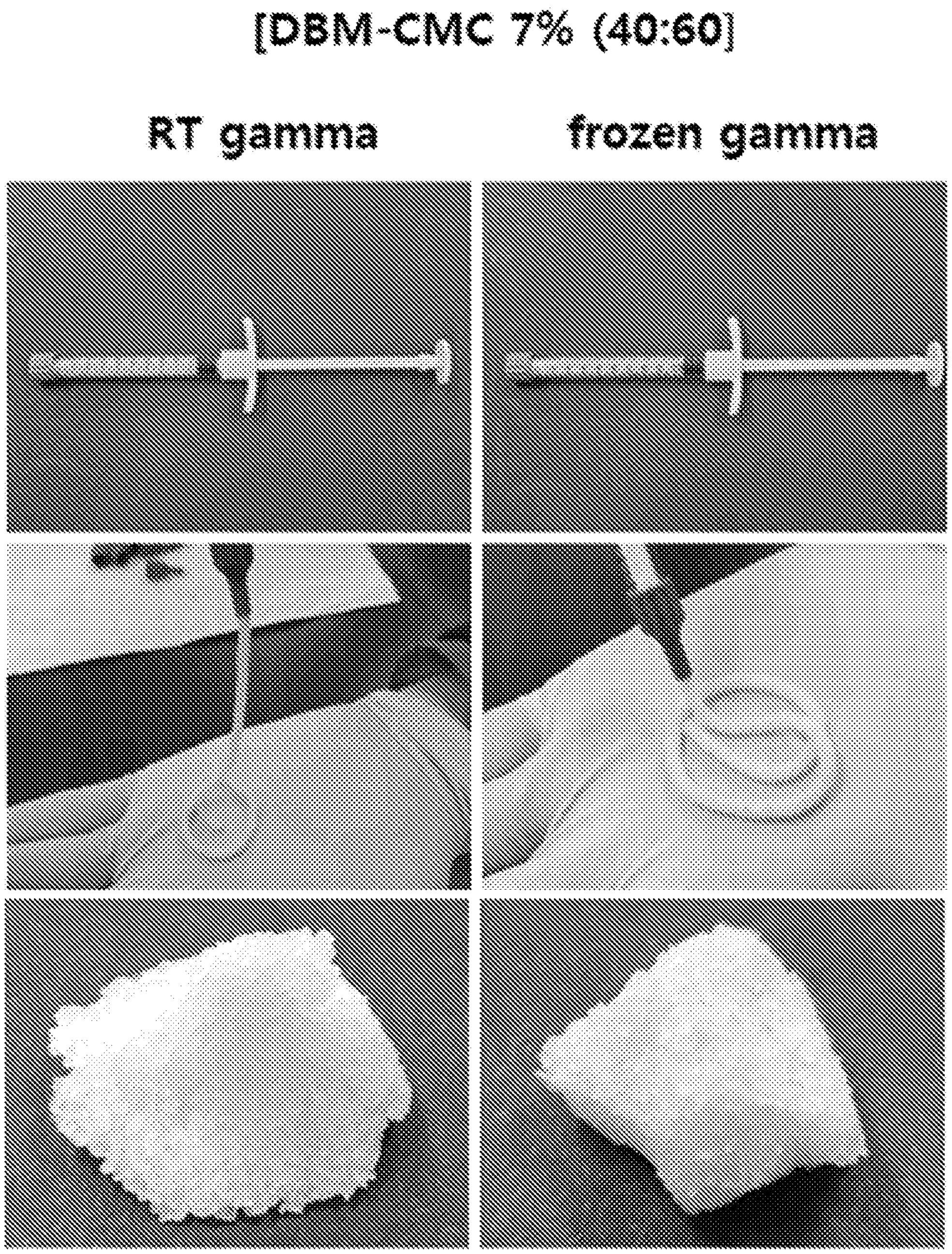
Figure 8:
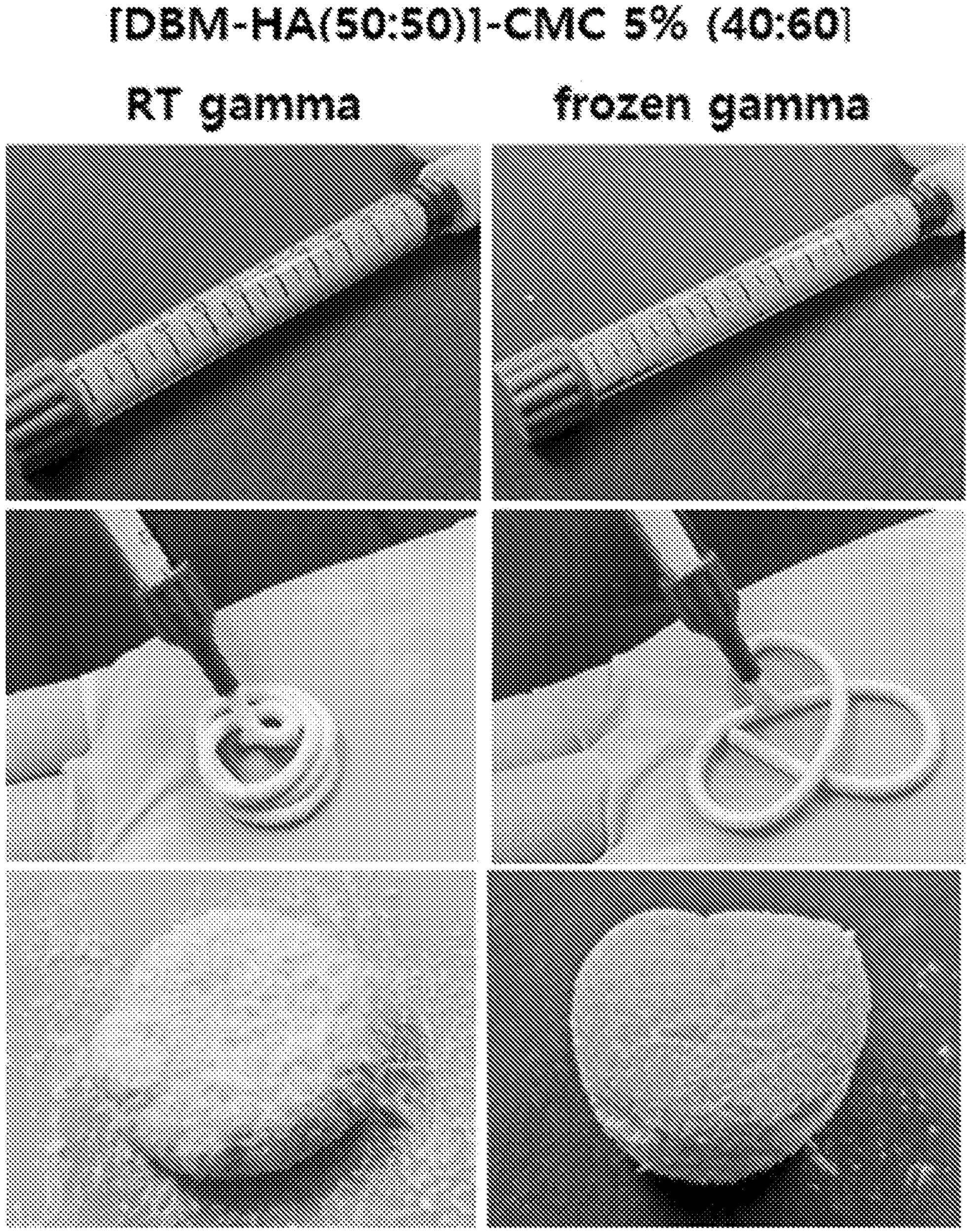
Figure 9:
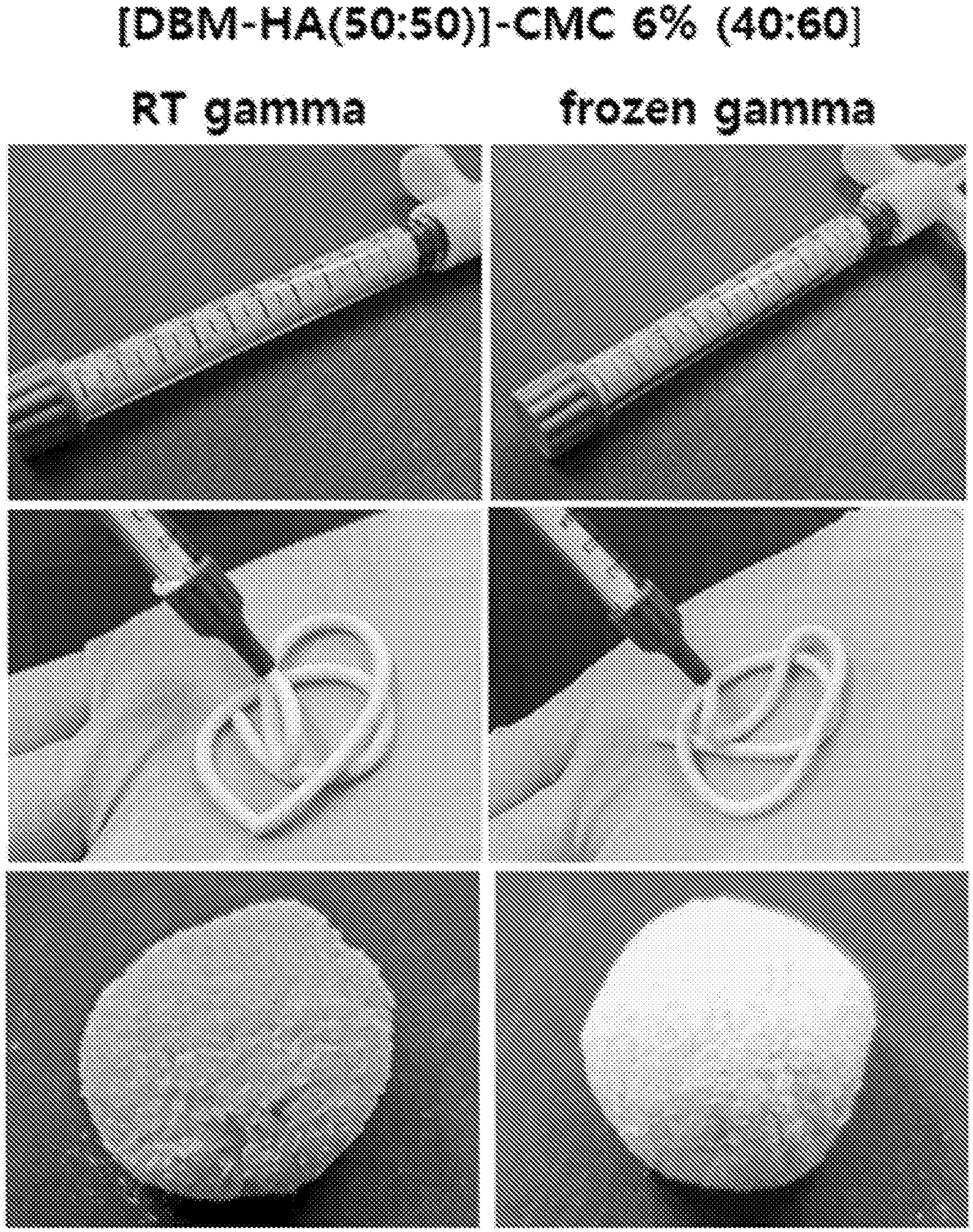
Figure 10:
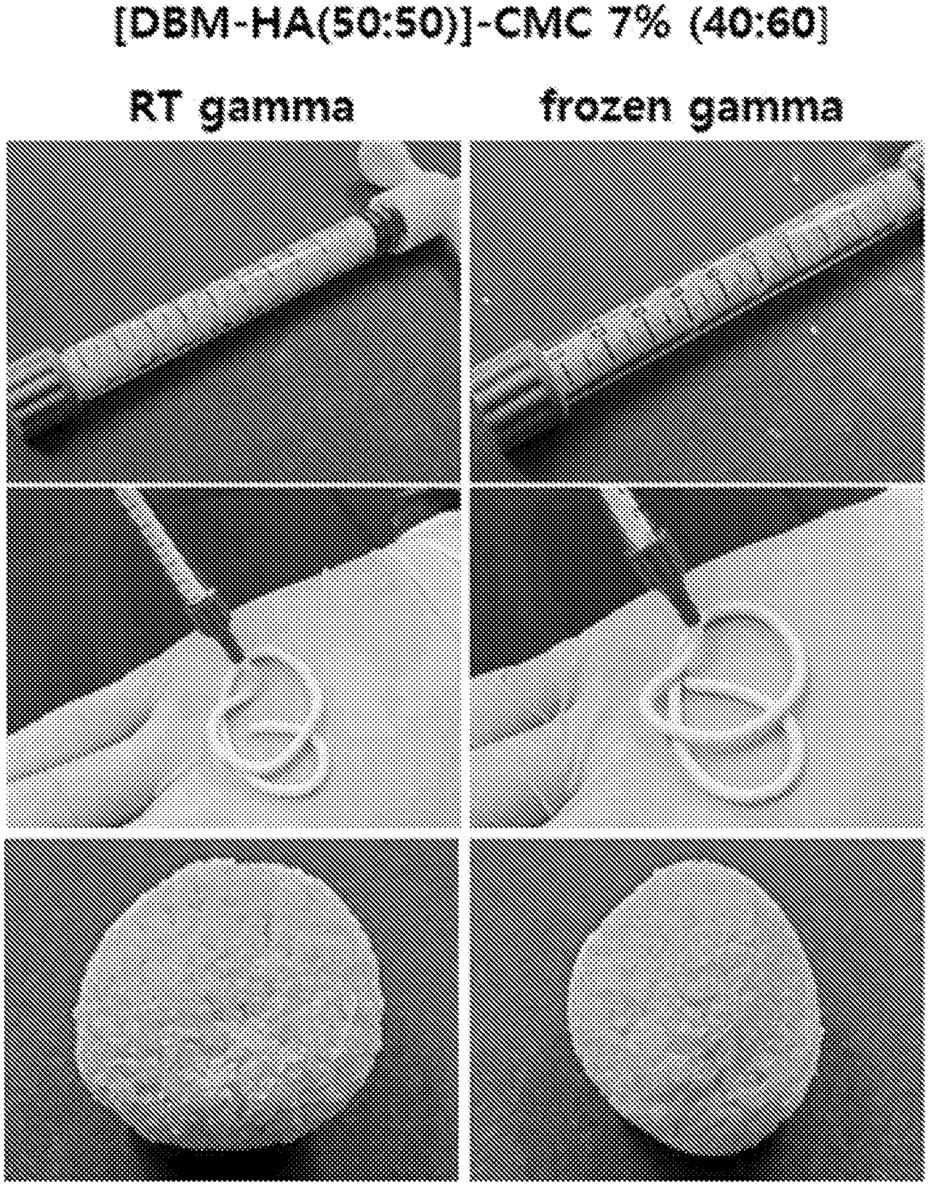

Hereinafter, the present invention will be described in more detail by examples. However, these examples are intended to illustrate the present invention by way of example, and the scope of the present invention is not limited by these examples. In addition, those skilled in the art will be able to make various changes and modifications to the present invention within a range that does not impair the spirit of the present invention. Terms not specifically defined herein should be understood to have meanings commonly used in the technical field to which the present invention belongs.

In the process of transplanting a bone graft material to a necessary site, it is required to minimize bone loss, to be easily changeable into any shape, and to be easily engrafted. To prepare a gel or putty type having these properties, sodium carboxymethyl cellulose (CMC), a material with excellent biocompatibility, was selected, and the mixing ratio varied by adjusting the concentration and quantity. In general, CMC is a semi-synthetic polymer obtained by partially substituting a hydroxyl group with an $OCH_2COONa$ group and dissolving in water, and is used for the purpose of improving emulsion stability.

Homogeneous demineralized bone matrix (DBM), hydroxyapatite, and sodium carboxymethyl cellulose (CMC) were each weighed with an electronic balance according to the weight ratios shown in Table 1 below, put into a mixer, and mixed until each material was uniformly mixed.

Specifically, in Examples 1 to 6, composite materials were prepared by mixing the demineralized bone matrix and CMC by concentration (2, 3, 4, 5, 6, 7 wt %) at a ratio of 40:60 wt %. In Examples 7 to 9, composite materials were prepared by mixing demineralized bone matrix and hydroxyapatite at a ratio of 50:50 wt %, and then mixing with CMC by concentration (5, 6, 7 wt %) at a ratio of 40:60 wt %.

TABLE 1

| | Group | DBM (wt %) | Hydroxyapatite (wt %) | CMC (wt %) | Water (wt %) |
|---|---|---|---|---|---|
| Example 5 | DBM-CMC 2% (40:60) | 40 | 0 | 1.2 | 58.8 |
| Example 2 | DBM-CMC 3% (40:60) | 40 | 0 | 1.8 | 58.2 |
| Example 3 | DBM-CMC 4% (40:60) | 40 | 0 | 2.4 | 57.6 |
| Example 4 | DBM-CMC 5% (40:60) | 40 | 0 | 3 | 57 |
| Example 5 | DBM-CMC 6% (40:60) | 40 | 0 | 3.6 | 56.4 |
| Example 6 | DBM-CMC 7% (40:60) | 40 | 0 | 4.2 | 55.8 |
| Example 7 | [DBM-HA(50:50)]-CMC 5% (40:60) | 25 | 25 | 3 | 57 |
| Example 8 | [DBM-HA(50:50)]-CMC 6% (40:60) | 25 | 25 | 3.6 | 56.4 |
| Example 9 | [DBM-HA(50:50)]-CMC 7% (40:60) | 25 | 25 | 4.2 | 55.8 |

The composite materials mixed at each mixing ratio according to Table 1 were prepared in a group stored at room temperature and a group frozen at −20° C. for 24 hours. 25 to 40 kGy of gamma irradiation was performed on the composites in each group.

Experimental Example 1. Evaluation of Properties of the Composition for Bone Regeneration When gamma irradiation is performed for sterilization, a problem arises in that the polymer chain of the composition for bone regeneration is broken down, which reduces physical properties such as viscosity. Since the originally expected physical properties of the composition for bone regeneration are altered, many problems are caused when such a composition for bone regeneration is transplanted to a target site such as an affected area.

Therefore, in this experiment, the handling characteristics of the composition before and after sterilization by gamma irradiation were compared. In particular, it was surprisingly successful to prove for the first time that the problem of physical property deterioration occurring with gamma irradiation sterilization can be solved if gamma irradiation sterilization is performed under freezing conditions.

After filling the syringe with the bone regeneration composition according to the mixing ratio prepared as in Examples 1 to 9, the composition was ejected by slowly pushing the syringe push rod with a hand. The ejected composition was scored according to the evaluation criteria in Table below for injectability (A), shape retention (B), agglomeration strength (C), and hand adhesion (D). Each physical property is divided into a total of five levels, from 0 to 4.

Injectability (A) indicates physical properties when the composition for bone regeneration is ejected from a syringe and injected into a transplant site. If the composition is ejected in powder form and cannot be properly injected into the transplant site, the score is evaluated as 0. If it is ejected from the syringe without breaking or cracking and is easily injected into the transplant site, the score is evaluated as 4.

Shape retention (B) indicates physical properties of whether the composition for bone regeneration can be deformed while maintaining its shape. If the composition for bone regeneration flows down when ejected from the syringe, the score is evaluated as 0. If it is ejected from the syringe without breaking or cracking and its shape can be changed during or after being injected into the implantation site, the score is evaluated as 4.

Agglomeration strength (C) indicates physical properties related to the cohesion of the composition for bone regeneration. If the composition for bone regeneration flows down without aggregation, the score is evaluated as 0. If it has strong cohesion and is well aggregated, the score is evaluated as 4.

The degree of hand adhesion (D) indicates physical properties related to whether a part of the composition for bone regeneration is separated when it adheres to a user's hand or a device corresponding thereto. When the composition for bone regeneration adheres to the hand, the score is evaluated as 0 if small substances, fibers, etc. are separated and come out, and in particular, flow down, whereas the score is evaluated as 4 if there is little material that comes out.

TABLE 2

| Score | Injectability (A) | Shape retention (B) | Agglomeration strength (C) | Hand adhesion (D) |
|---|---|---|---|---|
| 4 | Easy to inject and does not split during ejection | Able to change shape without breaking or splitting | Rigid due to strong cohesive force | Does not stick to hands |
| 3 | Easy to inject but breaks and splits during ejection | Agglomerate but some breaks and splits during changing shape | Moderately rigid | Small amount of material sticks to hands |
| 2 | Ejects in broken form | Does not agglomerate after breaking | Soft due to weak cohesive force | Large amount of material sticks to hands |
| 1 | Ejects but flows down | Does not agglomerate | Does not agglomerate | Large amount of material and fiber stick to hands |
| 0 | Ejects in powder form | Flows down | Flows down | Flows down |

The higher the score in Table 2, the more advantageous the bone regeneration composition is for implantation. That is, when the composition for bone regeneration with a high score is transplanted to a necessary site, it is well aggregated with strong cohesive force, has excellent properties of maintaining its shape, and does not come off easily on hands or devices, thereby minimizing bone loss. In addition, the fact that it can be easily changed into any shape can provide a very advantageous point to a user such as a doctor because the shape can be flexibly modified to suit the implantation site. In addition, the advantage that it can be engrafted in an intact form is also provided.

The compositions for bone regeneration prepared in Examples 1 to 9 were evaluated according to Table 2, respectively, in a non-sterilized state, in a state of gamma sterilization at room temperature, and in a state of gamma sterilization after freezing. The scores are shown in Tables 3 to 7, and shown graphically in FIG. 1. In order to maximize objectivity in the scoring evaluation, a total of ten experts including the inventors evaluated independently through a blind test, and then an average value of scores was obtained.

TABLE 3

| | Injectability (A) | | |
|---|---|---|---|
| | Before sterilization | After gamma sterilization at room temperature | After freezing and gamma sterilization |
| Example 1 | 4.0 | 1.0 | 3.0 |
| Example 2 | 4.0 | 1.7 | 4.0 |
| Example 3 | 4.0 | 3.0 | 4.0 |
| Example 4 | 4.0 | 3.0 | 4.0 |
| Example 5 | 3.7 | 3.0 | 4.0 |
| Example 6 | 3.7 | 3.3 | 4.0 |
| Example 1 | 4.0 | 4.0 | 4.0 |
| Example 8 | 4.0 | 4.0 | 4.0 |
| Example 9 | 4.0 | 4.0 | 4.0 |

TABLE 4

| | Shape retention (B) | | |
|---|---|---|---|
| | Before sterilization | After gamma sterilization at room temperature | After freezing and gamma sterilization |
| Example 1 | 4.0 | 0.0 | 3.0 |
| Example 2 | 3.7 | 1.0 | 3.3 |
| Example 3 | 3.7 | 2.3 | 3.7 |
| Example 4 | 3.7 | 3.0 | 3.7 |
| Example 5 | 3.7 | 3.0 | 3.7 |
| Example 6 | 4.0 | 3.0 | 3.0 |

TABLE 4-continued

| | Shape retention (B) | | |
|---|---|---|---|
| | Before sterilization | After gamma sterilization at room temperature | After freezing and gamma sterilization |
| Example 7 | 3.7 | 3.0 | 4.0 |
| Example 8 | 3.7 | 3.0 | 4.0 |
| Example 9 | 4.0 | 3.0 | 3.7 |

TABLE 5

| | Agglomeration strength (C) | | |
|---|---|---|---|
| | Before sterilization | After gamma sterilization at room temperature | After freezing and gamma sterilization |
| Example 1 | 3.0 | 0.0 | 2.0 |
| Example 2 | 3.0 | 1.0 | 3.0 |
| Example 3 | 3.0 | 2.0 | 3.0 |
| Example 4 | 3.7 | 2.0 | 3.0 |
| Example 5 | 3.7 | 2.0 | 3.0 |
| Example 6 | 4.0 | 2.0 | 3.0 |
| Example 7 | 4.0 | 3.0 | 4.0 |
| Example 8 | 4.0 | 3.3 | 4.0 |
| Example 9 | 4.0 | 3.0 | 4.0 |

TABLE 6

| | Hand adhesion (D) | | |
|---|---|---|---|
| | Before sterilization | After gamma sterilization at room temperature | After freezing and gamma sterilization |
| Example 1 | 3.3 | 0.0 | 2.0 |
| Example 2 | 3.0 | 1.0 | 3.0 |
| Example 3 | 4.0 | 2.0 | 3.0 |
| Example 4 | 4.0 | 3.0 | 4.0 |
| Example 5 | 4.0 | 2.0 | 3.0 |
| Example 6 | 4.0 | 2.0 | 3.0 |
| Example 7 | 3.0 | 2.3 | 3.0 |
| Example 8 | 3.0 | 2.0 | 3.0 |
| Example 9 | 3.0 | 2.0 | 3.0 |

Even though a composition with excellent handling properties before gamma sterilization was selected, injectability, shape retention, agglomeration strength, and hand adhesion are all significantly deteriorated in the sample gamma-irradiated at room temperature compared to the non-gamma-irradiated sample. That is, when gamma irradiation is performed for sterilization, the originally intended physical properties of the bone graft material are altered and deteriorated, so that it cannot be properly used for transplantation. The reason for such a phenomenon is believed to be due to the breakage of polymer chains in the composition by gamma irradiation.

In contrast, the frozen gamma-irradiated sample is superior to the room temperature gamma-irradiated sample in terms of injectability, shape retention, agglomeration strength, and hand adhesion. Particularly, it should be noted that all the physical properties of the frozen gamma-irradiated sample were recovered to a similar level compared to the non-gamma-irradiated sample.

Such a result means that when gamma irradiation for sterilization is combined with a special condition of freezing, the original physical properties of the bone graft material can be maintained. Therefore, it can be used for the purpose of transplanting the bone graft material properly to a desired site.

Experimental Example 2. Viscoelasticity Test of Composition for Bone Regeneration Dental bone graft materials have physical properties such as ability to resist movement from a bone defect site, fluidity, and viscosity, and the results may vary greatly depending on the degree of bonding between the bone graft material and the excipient. In order to find the optimization of the mixing ratio of the bone graft material and the excipient, the rheological viscoelastic properties were examined.

A viscoelasticity test was performed on the bone regeneration compositions prepared in Examples 1 to 9 above.

Specifically, a Rotational Rheometer (TA instrument Ltd., ARES-G2) was used to measure the viscoelastic properties of the sample. In order to measure the viscoelasticity and confirm the change in viscosity depending on the change in shear rate, the sample was placed on a 25 mm plate under a controlled temperature of 25° C., and then the gap between the cone and the plate was approached to 1 mm. After checking that the residual stress disappeared, sinusoidal vibration input was applied with a frequency ranging from 0.001 to 100% at 10 Hz of vibration measurement on the plate, and the response characteristics appearing on the cone were measured to determine the storage and loss coefficients (G' and G"), and complex viscosity.

Complex viscosity, linear viscoelastic range, and storage and loss coefficient measurements provide information about the relative stiffness and structural stability of materials. In particular, the complex viscosity generally represents the flow properties of a material.

When performing rheological analysis, G' (storage modulus) is a value representing elasticity, that is, a physical property corresponding to a solid. The higher the value, the harder the gel and the greater the ability to resist deformation.

G" (loss modulus) is a value representing viscosity, that is, a physical property corresponding to a liquid, in a viscoelastic material. It may be interpreted that the lower the value, the closer it is relatively to a solid, and the higher the value, the closer it is relatively to a liquid.

Figure 11A:
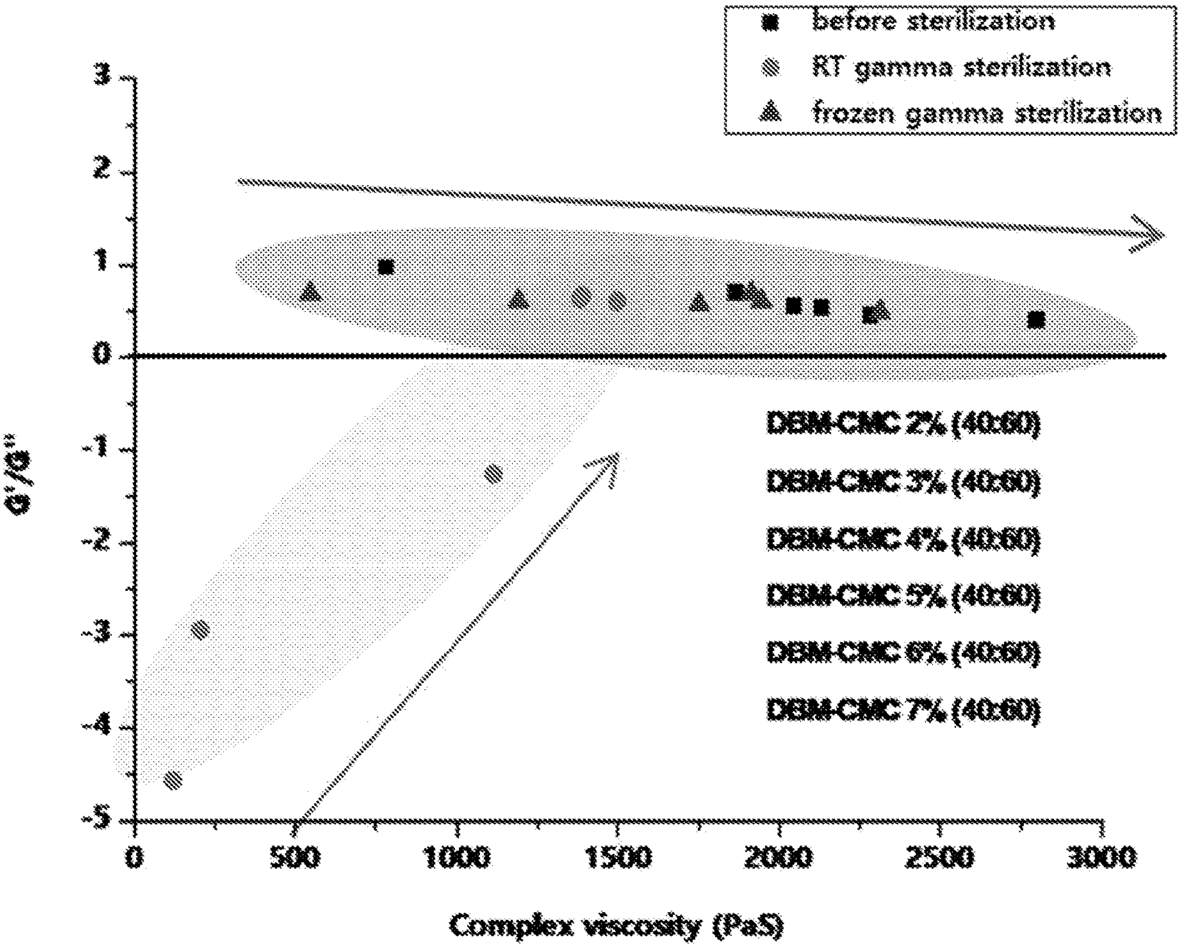
FIGS. 11*a* and 11*b* are graphs showing the result of determining the viscoelasticity of the samples prepared in Examples 1 to 9.
Figure 11B:
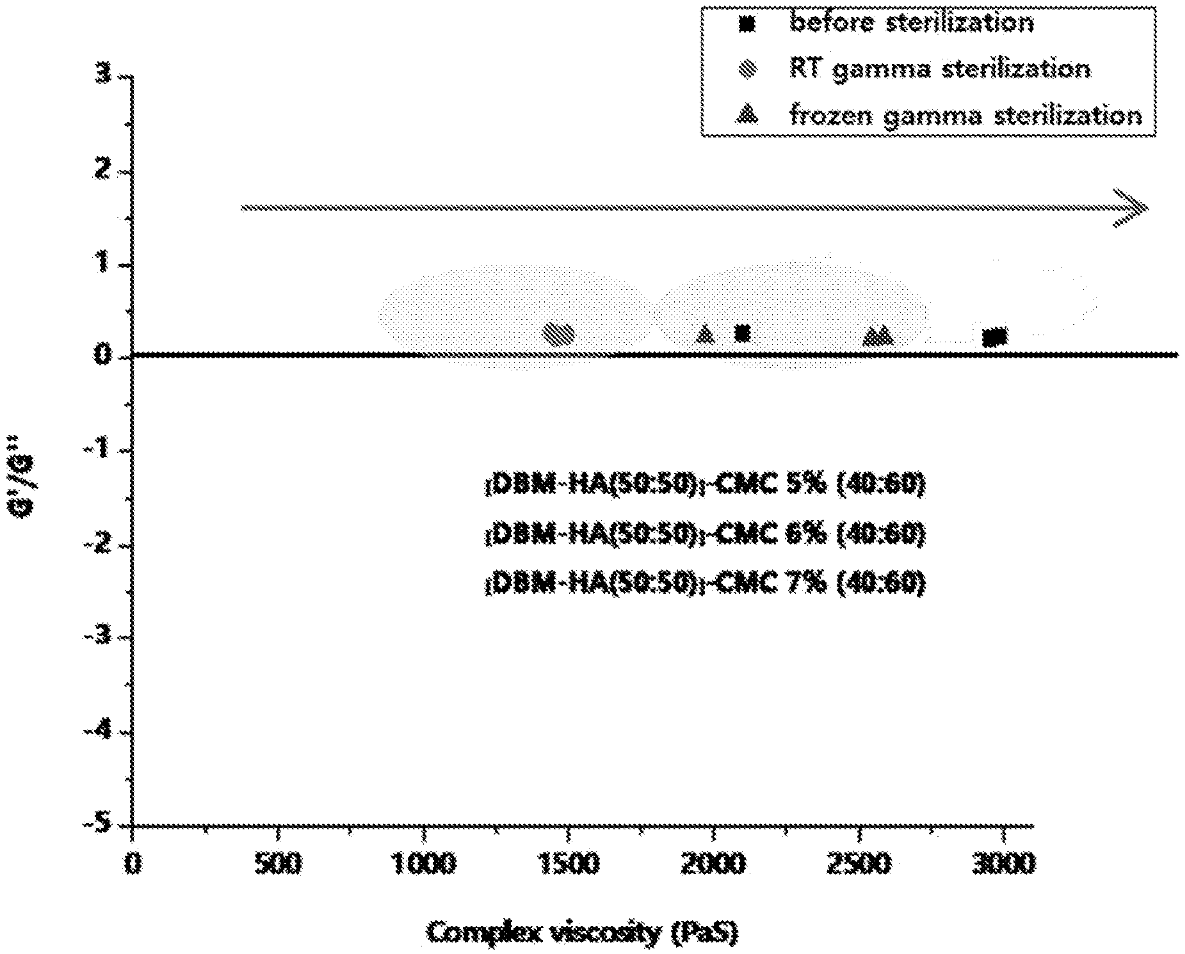

The results are shown in Tables 7 to 9, and the corresponding graphs are shown in FIGS. 11*a* and 11*b*.

TABLE 7

| | Before sterilization | |
|---|---|---|
| | Complex viscosity (Pa · s) | G'/G" |
| Example 1 | 781 | 0.97 |
| Example 2 | 1,865 | 0.70 |
| Example 3 | 2,044 | 0.56 |
| Example 4 | 2,132 | 0.54 |
| Example 5 | 2,283 | 0.45 |
| Example 6 | 2,799 | 0.40 |
| Example 7 | 2,101 | 0.26 |
| Example 8 | 2,985 | 0.23 |
| Example 9 | 2,951 | 0.21 |

| | After gamma sterilization at room temperature | |
|---|---|---|
| | Complex viscosity (Pa · s) | G'/G" |
| Example 1 | 120 | −4.57 |
| Example 2 | 204 | −2.94 |
| Example 3 | 1,113 | −1.26 |
| Example 4 | 1,383 | 0.63 |
| Example 5 | 1,388 | 0.66 |
| Example 6 | 1,497 | 0.60 |
| Example 7 | 1,457 | 0.22 |
| Example 8 | 1,493 | 0.25 |
| Example 9 | 1,440 | 0.28 |

TABLE 9

| | After freezing and gamma sterilization | |
|---|---|---|
| | Complex viscosity (Pa · s) | G'/G" |
| Example 1 | 547 | 0.69 |
| Example 2 | 1,751 | 0.58 |
| Example 3 | 1,190 | 0.61 |
| Example 4 | 1,912 | 0.69 |
| Example 5 | 1,943 | 0.61 |
| Example 6 | 2,313 | 0.49 |
| Example 7 | 1,971 | 0.23 |
| Example 8 | 2,545 | 0.21 |
| Example 9 | 2,586 | 0.22 |

As a result of analyzing the rheological characteristics for each concentration of CMC before sterilization, the higher the concentration of CMC, the higher the stiffness while the flowability is relatively reduced. In addition, a result of analyzing the rheological characteristics of the composition before sterilization depending on the mixing ratio of demineralized bone matrix and hydroxyapatite and the mixing ratio by concentration of CMC shows that the flowability decreased as the concentration of CMC increased, and that the higher the ratio of hydroxyapatite in the mixing ratio of the demineralized bone matrix and hydroxyapatite, the higher the flowability. Stiffness was observed to be similar in all groups.

After selecting groups with excellent handling characteristics before gamma sterilization, the rheological properties of the samples irradiated with gamma at room temperature and the samples irradiated with gamma after being frozen at −20° C. for 24 hours were analyzed. As a result, among the composite materials sterilized by gamma irradiation at room temperature, the composite materials (i.e., Examples 1 to 3) mixed up to a ratio of DBM-CMC 4% (40:60) had a negative G'/G" ratio, which means that the physical properties relatively corresponding to the liquid appear.

On the other hand, it was confirmed that frozen samples subjected to gamma irradiation exhibit viscoelasticity similar to that of samples before gamma sterilization.

The room-temperature gamma-irradiated sample showed a lower complex viscosity than the frozen gamma-irradiated sample, which is considered to be because the polymer chain was broken and could not maintain its shape. Therefore, based on these results, it can be concluded that pre-freezing is necessary to maintain rheological properties in the case of gamma irradiation.

Experimental Example 3. Physical Property Test of Composition for Bone Regeneration The physical properties of the composition for bone regeneration were compared depending on the mixing ratio of demineralized bone matrix and CMC.

Specifically, the demineralized bone matrix and CMC were each weighed with an electronic balance according to the weight ratios in Table 10, put into a mixer, and mixed until each material was uniformly mixed. In Comparative Examples 1 and 2, composite materials were prepared by mixing demineralized bone matrix and 5 wt % CMC at a ratio of 80:20 wt % or 60:40 wt %.

TABLE 10

| | Group | DBM (wt %) | Hydroxyapatite (wt %) | CMC (wt %) | Water (wt %) |
|---|---|---|---|---|---|
| Comparative Example 1 | DBM-CMC 5% (80:20) | 80 | 0 | 1 | 19 |
| Comparative Example 2 | DBM-CMC 5% (60:40) | 60 | 0 | 2 | 38 |

Figure 12:
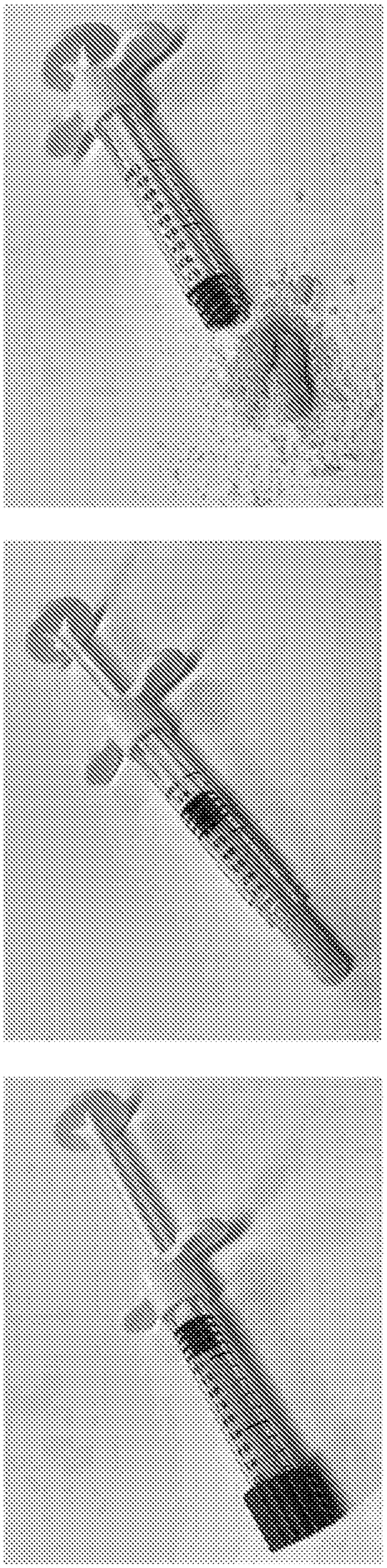
FIGS. 12 and 13 are photographs showing, in order, the state filled in the syringe, the state being ejected from the syringe, and the state after ejected from the syringe, respectively, for the samples prepared in Comparative Examples 1 and 2.
Figure 13:
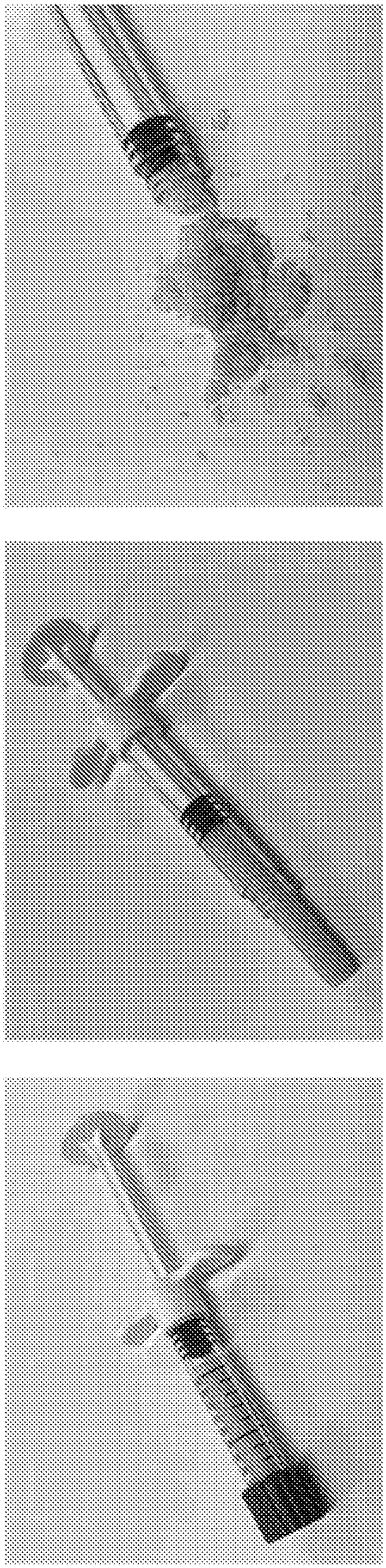

Then, the physical properties of the bone regeneration composition for each mixing ratio were analyzed by the method according to Experimental Example 1, and the results are shown in FIGS. 12 and 13

As a result, the composition for bone regeneration, in which the demineralized bone matrix and CMC were mixed at 80:20 wt % to 60:40 wt %, has remarkably reduced aggregation strength, injectability and shape retention. It is confirmed that it was not prepared in a form capable of bone grafting.

This result means that a material optimized for bone grafting can be obtained only when the demineralized bone matrix and CMC are mixed at a ratio of 40:60 wt % according to Examples 1 to 9.

What is claimed is:

1. A method for sterilizing a bone graft material, comprising:

a) preparing a bone graft material by mixing a demineralized bone matrix: a mixture of carboxymethyl cellulose salt and water in a weight ratio of 40:60;

b) pretreating the bone graft material prepared in step a) by maintaining it at a temperature of −20° C. or less; and c) sterilizing the bone graft material pretreated in step b) by gamma irradiation in 25 to 40 kGy;

wherein the sterilized bone graft material exhibits at least one of the following properties:

injectable and does not split during ejection from a syringe;

able to change shape without breaking or splitting;

rigid due to strong cohesive force; and does not stick to hands.

2. The method according to claim 1, wherein the bone graft material of step a) further comprises hydroxyapatite.

3. The method according to claim 2, wherein the bone graft material of step a) comprises a mixture of demineralized bone matrix and hydroxyapatite: a mixture of carboxymethyl cellulose salt and water in a weight ratio of 40:60.

4. The method according to claim 1, wherein the carboxymethyl cellulose salt in step a) is sodium carboxymethyl cellulose.

5. A method for sterilizing a bone graft material, comprising:

a) preparing a bone graft material by mixing a demineralized bone matrix: a mixture of carboxymethyl cellulose salt and water in a weight ratio of 40:60; wherein the carboxymethyl cellulose salt comprises 2-7% weight of the mixture of carboxymethyl cellulose salt and water;

b) pretreating the bone graft material prepared in step a) by maintaining it at a temperature of −20° C. or less; and c) sterilizing the bone graft material pretreated in step b) by gamma irradiation in 25 to 40 kGy.

* * * * *